United States Patent [19]

Jänkävaara

[11] Patent Number: 5,267,586
[45] Date of Patent: Dec. 7, 1993

[54] SHUTOFF VALVE MECHANISM FOR THE ORAL EVACUATOR OF A DENTAL UNIT

[75] Inventor: Jorma Jänkävaara, Järvenpää, Finland

[73] Assignee: Planmeca Oy, Finland

[21] Appl. No.: 973,165

[22] Filed: Nov. 6, 1992

[30] Foreign Application Priority Data

Nov. 8, 1991 [FI] Finland .................. 915275

[51] Int. Cl.$^5$ .................. E03B 5/00
[52] U.S. Cl. .................. 137/565; 251/342; 251/349; 433/95
[58] Field of Search .................. 137/565; 251/342, 348, 251/349, 354; 433/95

[56] References Cited

U.S. PATENT DOCUMENTS

| | | | |
|---|---|---|---|
| 1,418,592 | 6/1922 | McGee | 251/342 |
| 2,149,584 | 3/1939 | Davis | 251/342 |
| 2,785,016 | 3/1957 | Vollertzen et al. | 251/342 |
| 3,476,144 | 11/1969 | Krantz | . |
| 4,015,336 | 4/1977 | Johnson | 433/95 |
| 4,081,176 | 3/1978 | Johnson | 251/342 |
| 4,215,476 | 8/1980 | Armstrong | 433/95 |
| 4,356,998 | 11/1982 | Bach | 251/354 |
| 4,501,409 | 2/1985 | Hill | 251/354 |

FOREIGN PATENT DOCUMENTS

| | | |
|---|---|---|
| 91850013.3 | 9/1991 | European Pat. Off. . |
| 815880 | 10/1951 | Fed. Rep. of Germany ...... 251/342 |
| 2654784 | 7/1977 | Fed. Rep. of Germany . |
| 1500987 | 2/1978 | United Kingdom . |
| 1551429 | 8/1979 | United Kingdom . |

*Primary Examiner*—A. Michael Chambers
*Attorney, Agent, or Firm*—Jones & Askew

[57] ABSTRACT

The invention concept is a shutoff valve mechanism (40) for use in conjunction with the oral evacuator of a dental unit, said mechanism being connectable to a suction tube (14) communicating with a vacuum pump. The shutoff valve mechanism (40) comprises a valve (42, 48) by means of which an air flow (S) induced by the vacuum applied to the suction tube (14) can be switched on to effect via an evacuator tip (30) attached to the shutoff valve mechanism (40), whereby the evacuator tip can be employed for evacuating liquids and solid particles (SP) from the patient's mouth. The shutoff valve mechanism (40) further comprises non-moving elements (41, 42, 43, 44, 45, 46) permanently attached to the suction tube (14) and elements (49, 50, 51, 52, 53, 54, 55) adapted movable relative to said non-moving elements, both sets of elements incorporating a flow channel (41a, 42a, 43a, 53a).

10 Claims, 3 Drawing Sheets

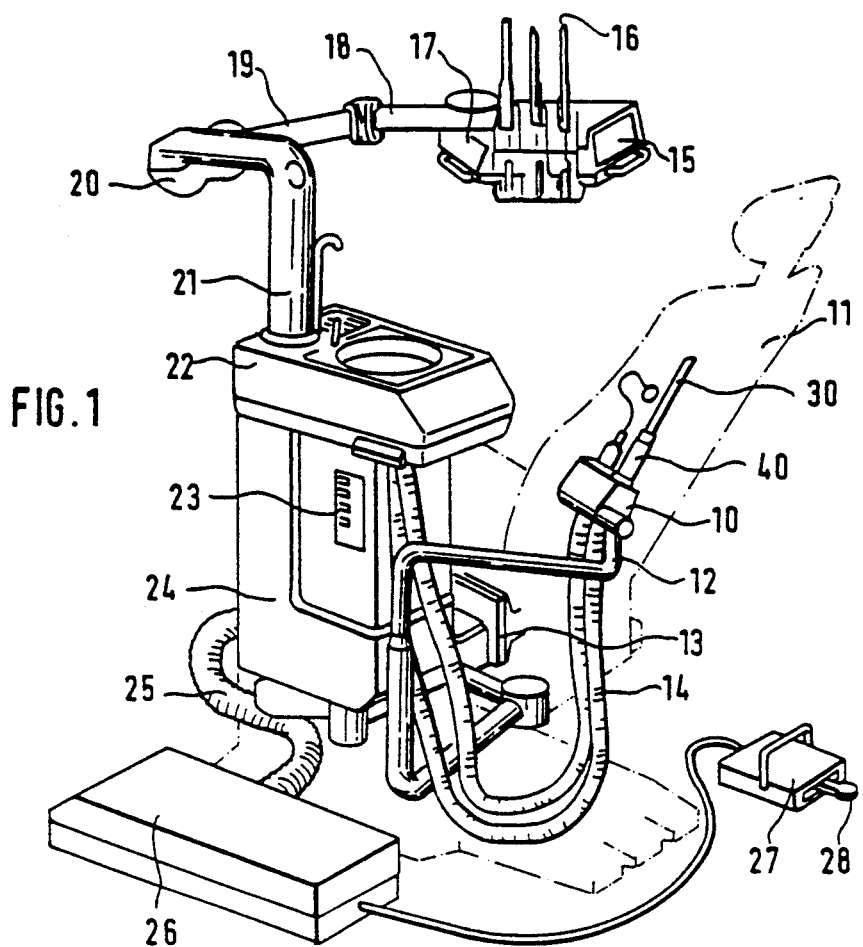
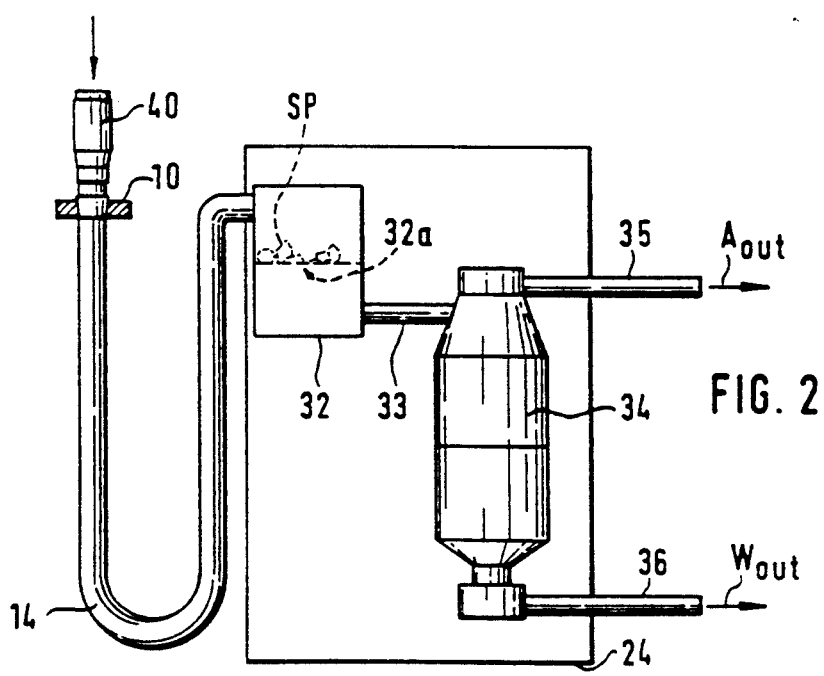

SHUTOFF VALVE MECHANISM FOR THE ORAL EVACUATOR OF A DENTAL UNIT

The invention relates to a shutoff valve mechanism for the oral evacuator employed in conjunction with dental units, said shutoff mechanism being attached to a suction tube connected to a vacuum pump, whereby the suction tube is used for evacuating liquids and solid particles from the patient's mouth, said shutoff valve mechanism comprising non-moving elements attached to the suction tube and elements adapted to be movable relative to the non-moving elements, the sets of elements incorporating a flow channel and said latter set of movable elements further being attached to the body part of the shutoff mechanism, which body part can accommodate the mounting of a suction tip for the oral evacuator, said shutoff mechanism incorporating a valve comprising a valve element and a compatible seating element, and said valve closing and staying closed by virtue of vacuum maintained in the suction tube, and said shutoff valve mechanism incorporating an articulated joint assembly capable of opening the shutoff valve mechanism by rotation about an axis or axes oriented nonparallel with the center axis of the shutoff valve mechanism.

A number of different types of shutoff valve mechanisms for the evacuators of dental units are known in the art. Conventional dental units incorporate suction tubes having one end equipped with a combination hand-held evacuator handpiece/shutoff valve mechanism and the other end connected to a filter which further communicates with a vacuum source and a collector unit for the removal of liquids. The evacuator handpiece is employed for evacuating saliva, water and solid particles such as tooth chips from drilling or amalgam debris. Solid particles are caught by the primary filter of the above-mentioned collector unit, while the liquids and air pass through the filter.

Dental units are conventionally equipped with such shutoff valve mechanisms in which the valve assembly is integrally mounted to the vacuum system incorporated in the central unit of the dental unit. These conventional valve assemblies generally use a membrane valve actuated by a magnetic valve, mechanical valve or similar actuator. The magnetic valve can be switched on and off by a microswitch or similar sensing element so that, for instance, when the evacuator handpiece, which is mounted to the end of a suction tube, is inserted into its holder, the microswitch or equivalent sensing element issues a control pulse and the magnetic valve switches the vacuum on or off. Such an arrangement is complex, and the membrane valves are prone to damage by sharp solid particles such as, e.g., tooth chips and amalgam clumps.

For the current state of the art concerning the invention, exemplifying reference is made to U.S. Pat. Nos. 4,522,592, 4,589,869, 4,799,885 and 4,861,266 as well as the EP patent publication 254,687 (corresponding U.S. Pat. No. 4,787,846). The above-mentioned patents disclose such comparable shutoff valve mechanisms which are placed at the distal end of the suction tube for direct actuation without a remote-controlled intermediate actuator. These shutoff valve mechanisms are capable of immediately switching the vacuum on and off, but they are generally clumsy and have a complicated construction.

Moreover, such a shutoff valve mechanism is known in the art in which the automatic activation of the vacuum function is sensed from the position of the evacuator handpiece. This shutoff valve mechanism has a mercury switch in the evacuator handpiece that gives an activation pulse via a control line to a valve located in the vacuum system of the central unit of the dental unit. Also this arrangement has remained lacking in both its construction and function.

Prior-art shutting mechanisms of vacuum tubes are limited by several drawbacks, which initiated the need for further development resulting in the present invention. These drawbacks have been associated with the special actions necessary for opening and closing the shutoff valve mechanism that impede and complicate the dentist's or assistant's work.

It is an object of the present invention to achieve a simple shutoff valve mechanism which performs reliably and is fast and easy to use by the dentist and/or assistant. The invention aims to provide such a shutoff valve mechanism which operates without remote control and associated microswitches and magnetic valves.

The attainment of above-defined goals has been attempted by a shutoff valve mechanism disclosed in the FI Patent application 900,995 (laid-open publication no. 85102), filed by the applicant of the present invention, said shutoff valve mechanism comprising non-moving elements permanently attached to the suction tube and elements adapted movable relative to the non-moving elements. A spring or springs is/are adapted between the movable and non-moving elements so that the spring(s) keeps (keep) the shutoff valve mechanism stable in the open position when the shutoff valve mechanism is removed from its holder. As the evacuator is returned into its holder, the collar or similar member of the collar causes the movable elements of the shutoff valve mechanism to be aligned relative to the non-moving elements of the mechanism so that a valve plate located between the movable and non-moving elements closes the valve by the weight of the suction tube and the non-moving elements acting against the spring-inducted counter force.

It is an object of the present invention to further develop the shutoff valve mechanism disclosed in the above-cited FI patent 900,995 so that a shutoff mechanism of simpler structure, easier use and of such construction is attained that offers a reliable operation even if the vacuum level and weight of the suction tubes employed vary in a relatively wide range.

It is a particular object of the invention to further improve the shutoff mechanism disclosed in the FI application cited above so that the mechanism would accommodate the use of relatively lightweight suction tubes such as the so-called RECTUS TM tube.

It is an object of the present invention to achieve such a shutoff mechanism in which the suction flow rate can be adjusted steplessly during the use of the evacuator by a single grasp without the need for regrasping the handpiece.

It is a further object of the invention to achieve such a shutoff mechanism in which the suction flow can be temporarily cut off during the treatment of the patient without the need for returning the evacuator handpiece into its holder.

It is moreover a further object of the invention to achieve said shutoff mechanism with such a construction which is self-cleaning and hygienic in use.

To attain the above-expressed and later disclosed goals, the invention is principally characterized in that, of the valve and seating elements of said shutoff valve structure, the first element is permanently attached to said valve body part and the second to the suction tube adapter, respectively, so that the shutoff mechanism can be comprised of two partial entities mutually rotatable about said rotation axis or axes, said partial entities being mutually adapted to provide a high lever arms ratio or long lever arm for the opening operation of the mechanism, thereby achieving a sufficient opening force actuated by the weight of the suction tube and/or flection force imposed.

The shutoff mechanism according to the invention achieves a high lever ratio or long lever arm for the opening motion of the mechanism and, thereby, a sufficient opening force for all operating situations, whereby the primary actuating force of the opening motion is the weight of the suction tube or flection force imposed so that a sufficient opening force can be developed even when using a relatively lightweight and flexible suction tube.

The mechanism according to the invention closes positively by the vacuum prevailing in the suction tube. As the mechanism according to the invention is opened by the mutual lateral displacement of the valve plate and its seating element, a further benefit is gained in that the valve is opened gradually and with a relatively low force so that the opening force need not abruptly overcome the entire counter force imposed by the vacuum prevailing in the suction tube as would be the matter if the valve plate should be moved axially with respect to center axis of the mechanism and the suction tube.

An important advantage of the invention is that the mechanism according to the invention permits a stepless control of the evacuating effect as necessary by a single grasp without the need for regrasping the handpiece and that the evacuation can be entirely switched off as necessary without placing the evacuator handpiece in its holder for this purpose.

The invention and its operating environment are next examined in greater detail by making reference to the figures of the attached drawing which illustrate diagrammatically a few exemplifying embodiments of the present invention, whereby the illustrating details must not be construed to limit the applications of the invention.

FIG. 1 shows in an axonometric view a dental unit to which the invention is applied.

FIG. 2 shows diagrammatically the vacuum system of the dental unit equipped with a shutoff valve mechanism according to the invention.

Figure 3A:
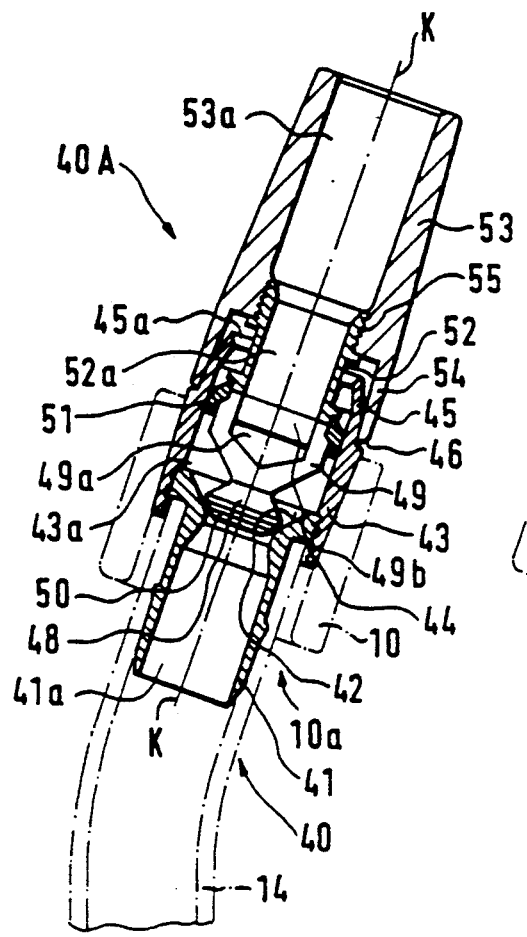
FIG. 3A shows the shutoff valve mechanism according to the invention with the evacuator handpiece inserted in its holder, whereby the suction flow is cut off by the valve mechanism.

The dental unit illustrated in FIG. 1 has a basically conventional construction so its function is described solely in an outlining manner to the end of explaining the background of the invention and to illustrate a possible application environment of the invention.

The dental unit shown in FIG. 1 comprises a central unit 24 incorporating the assistant's control panel 23 with a cuspidor tray unit 22 mounted above it. Above the central unit 24 is adapted a support column 21 carrying an articulated support arm 20. To the articulated support arm 20 is pivotally attached a movable arm 19 carrying a console support arm 18 pivotally attached at its end. The distal end of the console support arm 18 further carries a dentist's control panel 15 with instrument holder modules 16. The central unit 24 is connected via a support frame 13 to a patient chair 11. A holder 10 for suction tubes 14 is connected via a multijoint articulated arm 12 to the central unit 24. One of the suction tubes 14 has at its distal end a shutoff valve mechanism 40 according to the invention with a tubular evacuator tip 30 attached to the mechanism. The dental unit is provided with a junction box 26 which communicates with the central unit 24 via a conduit 25. To the junction box 20 is connected a foot-control box 27 which houses a control pedal 28.

As shown in FIG. 2, the central unit 24 of the dental unit incorporates a collection system 32 whose filter 32a separates solid particles SP. The collection system 32 is from the inlet side of the filter 32a connected via a pipe 33 to a collecting tank 34 whose lower part is provided with a drain pipe 36 for the drainage of liquids as indicated by arrow $W_{out}$. To the upper part of the collecting tank 34 is arranged a pipe 35 which in the direction of arrow $A_{out}$ is connected to a vacuum pump (not shown). Also such conventionally used systems are feasible in which the collecting tank is not adapted in the central unit, but rather, in an other part of the building in which the dental unit is housed, whereby such a collecting tank generally serves for several dental units simultaneously. To the upper part of the collection system 32 is connected a suction tube 14 having a shutoff valve mechanism 40 mounted to its distal end. The oral evacuator tip 30 attached to the inlet end of the shutoff valve mechanism 40 is employed for evacuating air froth, saliva, water and solid particles from the patient's mouth. Solid particles comprise, i.a., tooth and amalgam chips, which in prior-art constructions have caused damage to the membranes of valve mechanisms.

Figure 3B:
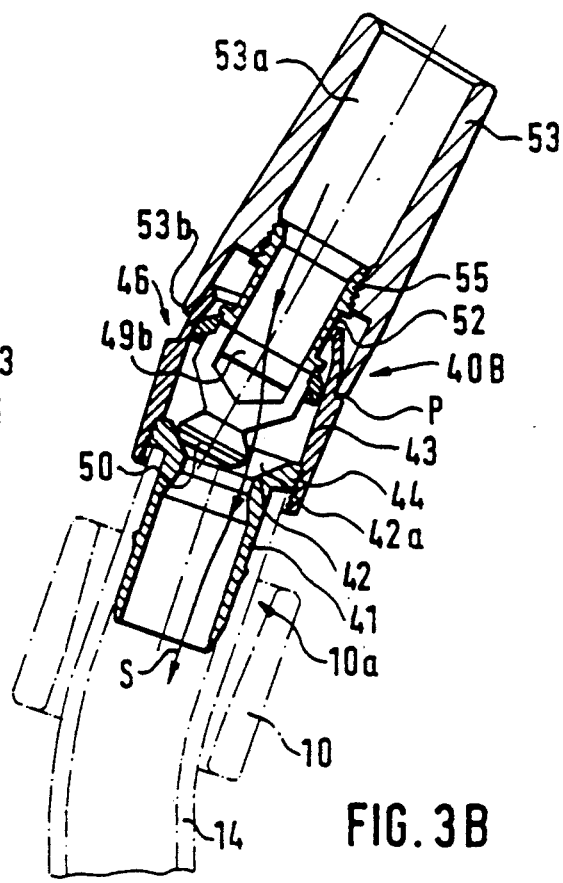
FIG. 3B shows an operating phase of the shutoff valve mechanism in which the mechanism is already partially opened when the evacuator handpiece is lifted from its holder.
Figure 3C:
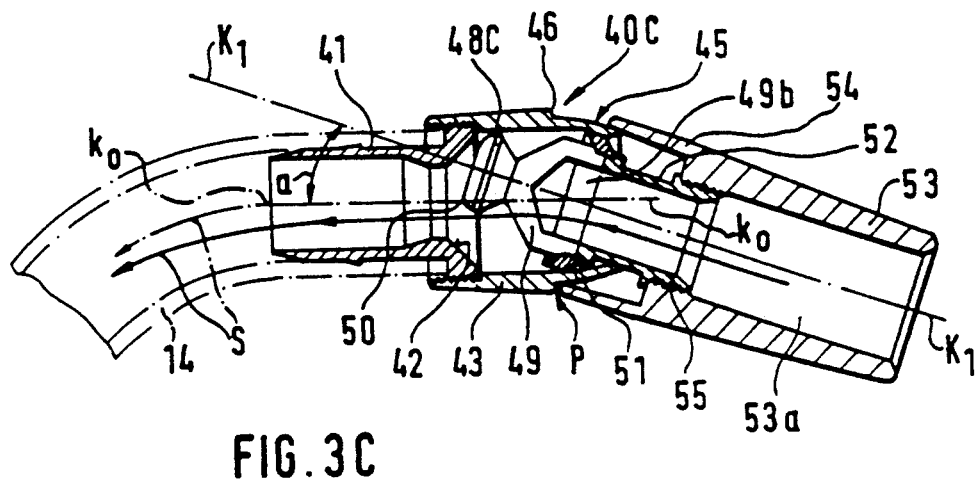
FIG. 3C shows the operating/open position of the shutoff valve mechanism in similar manner as illustrated in FIGS. 3A and 3B.

FIGS. 3A, 3B and 3C illustrate the structure and function of the shutoff valve mechanism 40 according to the invention. The mechanism comprises non-moving elements 41, 42, 43, 45 permanently attached to the suction tube 14, said elements incorporating a flow channel portion 41a, 42a, 43a. The elements 41, 43, 45 are mostly bodies of revolution with a cylindrical shape. The end of the suction tube 14 is placed onto an adapter element 41. The distal end of the adapter element 41 has a conical portion 42 which, together with the conical portion 50 of the valve plate 48, forms the cutoff section for the flow S. To the distal end of the adapter element 41 is mounted a bushing element 43 on threads 44. Extending from the distal end of said bushing element 43 is adapted an articulating portion 45 having its end essentially shaped spherical.

The shutoff valve mechanism 40 further comprises a cylindrical body part 53 whose conically tapered hole 53a is adapted to accommodate a tubular oral evacuator tip 30. To said body part 53 is mounted on inner threads 55 an inner bushing element 52 which has an annular element 49b of the valve plate 48 attached to it with the help of a plastic ring 51, whereby a pair of ribs supporting the valve plate 48 extend from said annular element. Together with the conically shaped seating portion 42 of the adapter element 41, the conically shaped portion 50 of the valve plate 48 form the flow cutoff section of the valve, which in the diagram of FIG. 3A is shown in the flow cutoff position. The proximal end of the body part 53 is extended with a thinner-walled annular bushing portion 54 ending at the body part edge 53b. The elements 49, 50, 51 and 52 are attached to the body part 53 by means of a threaded joint 55, thus causing them to tilt with the body part during the opening flection of the valve mechanism.

With the exception of the ribs 49, the elements of the shutoff valve mechanism are formed by rotation pieces whose center axis is indicated by line K—K in FIG. 3A.

When the shutoff valve mechanism 40 is brought to the closing position 40A illustrated in FIG. 3A, the elements permanently attached to the suction tube 14 and the elements permanently attached to the body part 53 are coaxially aligned to the center axis of the mechanism marked by line K—K in FIG. 3A. Then, the conical portion 50 of the valve plate 48 is capable of tightly mating with the conical seating portion 42 of the adapter element 41, and the cutoff state is maintained by the force imposed by the vacuum prevailing in the suction tube 14. The mating surfaces 42/50 are hard spherical or conical surfaces fabricated to a sufficiently high precision.

When placed out of use in the cutoff position, the shutoff valve mechanism 40A rests against a hole or slot 10a of a holder 10 mounted to the end of a support arm 12 so that the slightly conically tapering outer surface of the bushing element 43 permanently attached to the suction tube 14 mates with the correspondingly tapered inner surface of the hole or slot 10a. When the evacuator handpiece is taken from its holder, the user's hand grasps the body part 53 of the shutoff valve mechanism 40A and moves it to position 40B according to FIG. 3B so as to remove the handpiece containing the shutoff valve mechanism from its slot 10a and the elements permanently attached to the suction tube 14 and the body part 53, respectively, are displaced by rotation from each other, whereby the inner surface of the bushing element portion 54 glides over the outer surface of the articulating portion 45, and simultaneously, the outer edge of the ring 51 glides over the inner surface of the articulating portion 45 with a certain amount of play. As the evacuator is further moved from position 40B shown in FIG. 3C to the operating position 40C shown in FIG. 3C and FIG. 4, the valve is opened more by rotation essentially about axis P. When the shutoff valve mechanism reaches the fully open position illustrated in FIG. 3C, the outer edge 53b of the element 53 rests against the collar 46 of the element 43. The axis of rotation for the opening motion of the shutoff valve mechanism 40 need not always coincide with axis P, but in general, the axis of rotation is generally to the side of the center axis K—K and typically orthogonal to the center axis K—K.

An essential characteristic of the invention is that the opening motion of the shutoff valve mechanism 40 takes place about an axis of rotation which is oriented orthogonal to the center axis K—K of the mechanism so that the center axis $K_0$—$K_0$ of the elements attached to the suction tube 14 deviates from the center axis $K_1$—$K_1$ of the elements attached to the body part 53. In the fully open position 40C (FIG. 3C), the angle a between the axes $K_0$-$K_1$ typically is in the range a=10°...30°, preferably approx. 20°. The body part 53 can rotate freely with respect to the elements permanently attached to the suction tube 14. The joint formed between the portions 45 and 54 has a relative large amount of play thus preventing jamming of the mechanism in any of its operating positions. A slight amount of air leakage is permitted through the joint between the portions 45 and 54 which to keep the mating surfaces clean.

Opening of the mechanism 40 and subsequent disengagement of its different elements is prevented by virtue of the element 52 meeting the end surface of the articulating portion 45 in the position shown in FIG. 3C simultaneously with the end surface of the ring element 51 meeting the inner surface of the portion 45 and the edge portion 53b of the bushing element portion 54 meeting the collar 46 of the element 43. This arrangement secures a stable fully open position of the mechanism in the manner illustrated in FIG. 3C.

Figure 4:
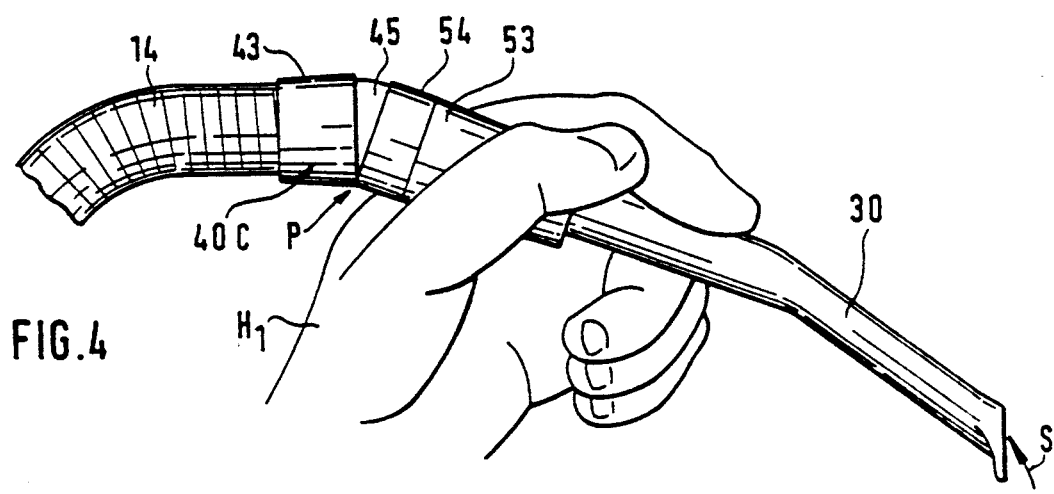
FIG. 4 shows the normal operating position and necessary grasp applied by the user for the shutoff valve mechanism and the evacuator tip attached to it.

FIG. 4 shows the normal operating position of the evacuator handpiece according to the invention, together with the grasp applied by the user's hand, in which the thumb and forefinger of the hand $H_1$ support the body part 53 of the mechanism 40C, while the middle finger supports from below the evacuator tip 30, whereby the shutoff valve becomes rotated to the open position illustrated in FIG. 3C by virtue of the weight of the suction tube 14 and the flection applied. Then, the evacuating vacuum flow S is activated through the evacuator tip 30.

Figure 5:
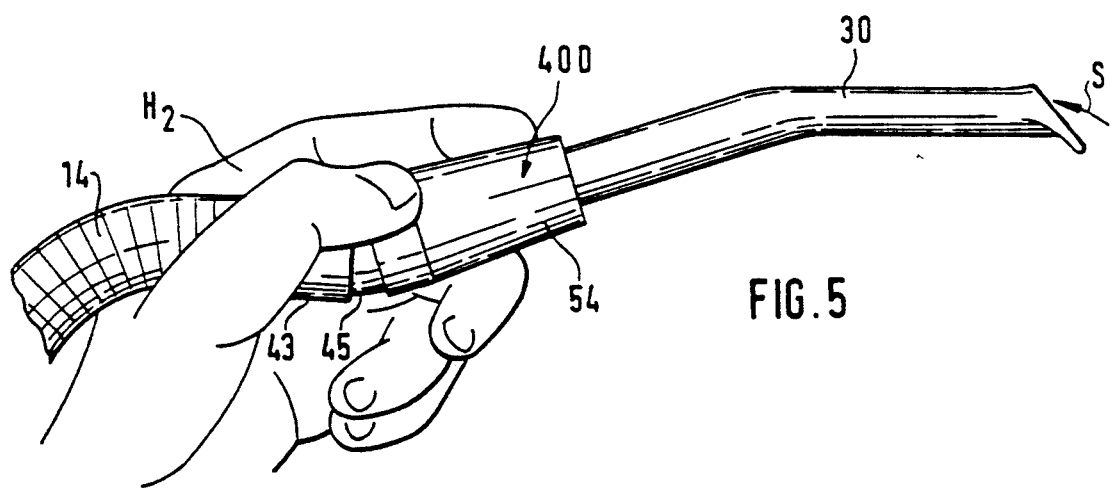
FIG. 5 shows another operating position and necessary grasp for the shutoff valve mechanism.

The shutoff valve mechanism can also be brought to the open position by supporting the end of the suction tube 14 and the element 43 attached to it as shown in FIG. 5 against the anatomical snuffbox, that is, the space between the thumb and the forefinger, simultaneously gripping the body part 53 by a grasp formed by the forefinger and middle finger and then flexing the mechanism to the open position 40D by pressing with the thumb, while simultaneously supporting the mechanism with the forefinger and the middle finger. As the thumb is released from the grasp illustrated in FIG. 5, the mechanism 40 closes automatically by the vacuum force of the suction flow.

The grasp illustrated in FIG. 5 also permits stepless control of the opening of the shutoff valve mechanism so that the evacuating effect and suction flow can be steplessly set to a desired level for the operating situation. This means that the mechanism according to the invention permits a full control of all possible positions of the shutoff valve mechanism between the fully open position (FIG. 3C) and fully closed position (FIG. 3A) without changing the grasp. An essentially important characteristic of the valve according to the invention is also therein that the valve of the evacuator handpiece can be temporarily closed during on-going treatment by straightening the handpiece in the grasp or lowering it onto a supporting platform without the need for returning the evacuator handpiece to its holder. This feature is most important to the flexibility and speed of the dentist's operation.

When the operation with the evacuator handpiece is concluded, the handpiece containing the shutoff valve mechanism 40 is placed in its holder 10 in the position 40A illustrated in FIG. 3A, whereby the shutoff valve mechanism is automatically closed and the suction flow S stopped.

As is evident from the description above, the shutoff valve mechanism 40 according to the present invention is characterized by a simple construction, ease of use and operational reliability, the latter characteristic essentially resulting from the fact that the shutoff valve mechanism 40 has two stable end positions, that is, the open position actuated by the weight of the suction tube 14 or a manually actuated flection, and the closed position actuated by vacuum force of the suction flow.

The above described arrangement achieves a shutoff valve mechanism of simple construction and reliable function with an automatic closing function by vacuum and a correspondingly automatic opening function at the grasping of the evacuator handpiece.

Furthermore, the shutoff valve mechanism according to the invention is flexible in use as illustrated by the exemplifying operating possibilities illustrated in FIGS. 4 and 5. An important benefit is also that the mechanism is closed by vacuum alone, which makes its closing independent from the weight of the suction tube. This feature makes the use of specially lightweight and flexible suction tubes possible, which contributes to easier operation by the evacuator handpiece.

Any reference in the above text and the subsequent claims to the center axis K—K of the shutoff valve mechanism 40 must be broadly understood to mean such a hypothetical axis which is longitudinally aligned to the center of the suction tube 14 as it is freely hanging and unflexed. This definition of the center axis does not necessarily require the shutoff valve mechanism to be perfectly symmetrical with respect to said center axis K—K. A final notice must be made to emphasize the fact that the axis of rotation of the articulating assembly during the opening or closing the shutoff valve mechanism 40 about its articulating element assembly need not necessarily be stationary, but rather, can be displaced and even reoriented during the different phases of the opening/closing operation.

The claims of the patent application are presented in the following, whereby the different details of the invention may be varied and modified from those of the exemplifying embodiments within the scope of the claims defining the invention.

We claim:

1. A shutoff valve mechanism (40) for use in conjunction with a oral evacuator of a dental unit, said mechanism being connectable to a suction tube (14) communicating with a vacuum pump, said shutoff valve mechanism (40) comprising non-moving elements (41, 42, 43, 44, 45, 46) permanently attached to the suction tube (14) and elements (49, 50, 51, 52, 53, 54, 55) adapted movable relative to said non-moving elements, both sets of elements incorporating a flow channel (41a, 42a, 43a, 53a) and the latter set (49, 50, 51, 52, 53, 54, 55) of elements being attached to a body part (53) of the shutoff valve mechanism capable of accommodating the connection of an evacuator tip (30) of the oral evacuator, said shutoff valve mechanism (40) further comprising a valve element (48) and a compatible seating element (42), and said valve closing and staying closed (FIG. 3A) by virtue of a vacuum maintained in the suction tube (14), and said shutoff valve mechanism further comprising an articulated joint assembly (45, 51, 54) capable of opening the shutoff valve mechanism by rotation about an axis or axes oriented nonparallel with the center axis (K—K) of the shutoff valve mechanism (40), characterized in that one (48/42) of the valve elements (48) and seating elements (42) is permanently attached to said body part (53), while the other element (42/48) is attached to the adapter member (41) of the suction tube (14) so that the shutoff valve mechanism incorporates two partial entities mutually rotatable about said rotation axis or axes, said partial entities being mutually adapted to provide a high lever arms ratio or long lever arm for the opening operation of the mechanism, thereby achieving a sufficient opening force actuated by the weight of the suction tube and/or flection force imposed.

2. A shutoff valve mechanism as defined in claim 1, characterized in that the shutoff valve (42/48) of the shutoff valve mechanism (40) during the use of the evacuator handpiece can be manually and without regrasping the evacuator handpiece steplessly controlled between the fully open position (FIG. 3C) and the fully closed position (3A) for the purpose of controlling the suction flow.

3. A shutoff valve mechanism as defined in claim 1, characterized in that the shutoff valve mechanism (40) incorporates a position in which the evacuating vacuum can be temporarily switched off during the treatment of the patient without the need for returning the shutoff valve mechanism (40) to its holder (10).

4. A shutoff valve mechanism as defined in claim 1, characterized in that the valve plate (48) of the shutoff valve is connected by ribs (49) to the body part (53) of the mechanism and that the seating element (42) adapted to mate with the valve plate (48) is connected to the adapter element (41) for the suction tube (14).

5. A shutoff valve mechanism as defined in claim 1, characterized in that the shutoff valve mechanism is comprises of elements that are bodies of revolution, primarily of cylindrical shape, whose center axis in the closed position (49A) of the mechanism coincides with the longitudinal axis (K—K) (FIG. 3A) of the shutoff valve mechanism.

6. A shutoff valve mechanism as defined in claim 1, characterized in that the shutoff valve mechanism comprises at the end of the adapter element (41) of the suction tube (14) such portion (42) with a conical or spherical surface of revolution that can act as the mating surface for the seating surface (50) fabricated on the valve plate (48), that a bushing element (43) with an articulating portion (45) at its outer end is mounted on the outer threads (44) of said adapter element (41), that a bushing element portion (54) of the body part (53) is adapted on said articulating portion (45) with a large amount of play, and that said body part (53) is adapted in an articulated manner to the elements attached permanently to the suction tube (14).

7. A shutoff valve mechanism as defined in claim 6, characterized in that the valve plate (48) is attached by its ribs (49) to an annular portion (49b), about which is adapted a mounting ring (51) that during the opening and closing of the valve glides along the inner surface of the articulating portion (45) of the bushing element (43) with a large amount of play.

8. A shutoff valve mechanism as defied in claim 7, characterized in that the valve plate (48) is attached by the ribs (49) and annular portion (49b) to an inner bushing element (52) which is mounted by outer threads (55) to the inner threads of the body part (53).

9. A shutoff valve mechanism as defined in claim 8, characterized in that between the shutoff valve mechanism (40) has a stable fully open position (FIG. 3C) which is limited by virtue of the outer surface of the inner bushing element (52) meeting the outer edge of the articulating portion (45), the outer surface of the annular portion (45) and/or the edge (53b) of the bushing element portion (54) of the body part (53) meeting the collar (46) of the bushing element (43).

10. A shutoff valve mechanism as defined in claim 6, characterized in at the between the bushing element (43) and the articulating portion (45) attached to it is provided a collar (46) which, together with the edge (53b) of the bushing element portion (54) of the body part (53), acts to limit the fully open position (40C, 40D) of the shutoff valve mechanism.

* * * * *